United States Patent [19]
Martinez

[11] Patent Number: 4,870,952
[45] Date of Patent: Oct. 3, 1989

[54] FIBER OPTIC ILLUMINATOR FOR USE IN SURGERY

[76] Inventor: Miquel Martinez, 2202 Apricot, Irvine, Calif. 92714

[21] Appl. No.: 546,414

[22] Filed: Oct. 28, 1983

[51] Int. Cl.⁴ .............................................. A61B 1/06
[52] U.S. Cl. ......................................... 128/23; 128/6; 128/395
[58] Field of Search ....................... 128/4–8, 128/23, 395–398, 303.1; 604/20

[56] References Cited

U.S. PATENT DOCUMENTS

| | | | |
|---|---|---|---|
| 3,131,690 | 5/1964 | Innis et al. ................................ | 128/6 |
| 3,285,242 | 11/1966 | Wallace .................................... | 128/23 |
| 3,357,423 | 12/1967 | Winchester et al. .................... | 128/23 |
| 3,674,013 | 7/1972 | Polyanyl .................................. | 128/6 |
| 3,699,950 | 10/1972 | Humphrey et al. ..................... | 128/23 |
| 3,760,797 | 9/1973 | Stauffer ................................... | 128/6 |
| 3,809,072 | 5/1974 | Ersek et al. ............................. | 128/23 |
| 4,222,375 | 9/1980 | Martinez ................................. | 604/20 |
| 4,248,214 | 2/1981 | Hannah et al. ......................... | 128/23 |

FOREIGN PATENT DOCUMENTS 2545355  4/1977  Fed. Rep. of Germany ........ 128/23

Primary Examiner—Max Hindenburg
Attorney, Agent, or Firm—Epstein, Edell & Retzer

[57] ABSTRACT

A fiber optic illuminator for use in surgery includes an adapter having a barrel to be received in a socket adjacent a light source, a body with a conical bore therein and a light conducting rod mounted in the barrel, an interconnector having as conical end received in the conical bore of the adapter to position a proximal end of a fiber optic element adjacent the light conducting rod, a support hub having a distal end mounting a cannula, and a length of flexible tubing connecting the interconnector and the support hub, the fiber optic element passing through the tubing, the support hub and the cannula and having a distal end positioned at the distal end of the cannula such that light from the light source is conducted to the distal end of the cannula via the light conducting rod and the fiber optic element. The fiber optic illuminator is designed to efficiently transmit light with little loss and to be economically disposable.

8 Claims, 2 Drawing Sheets

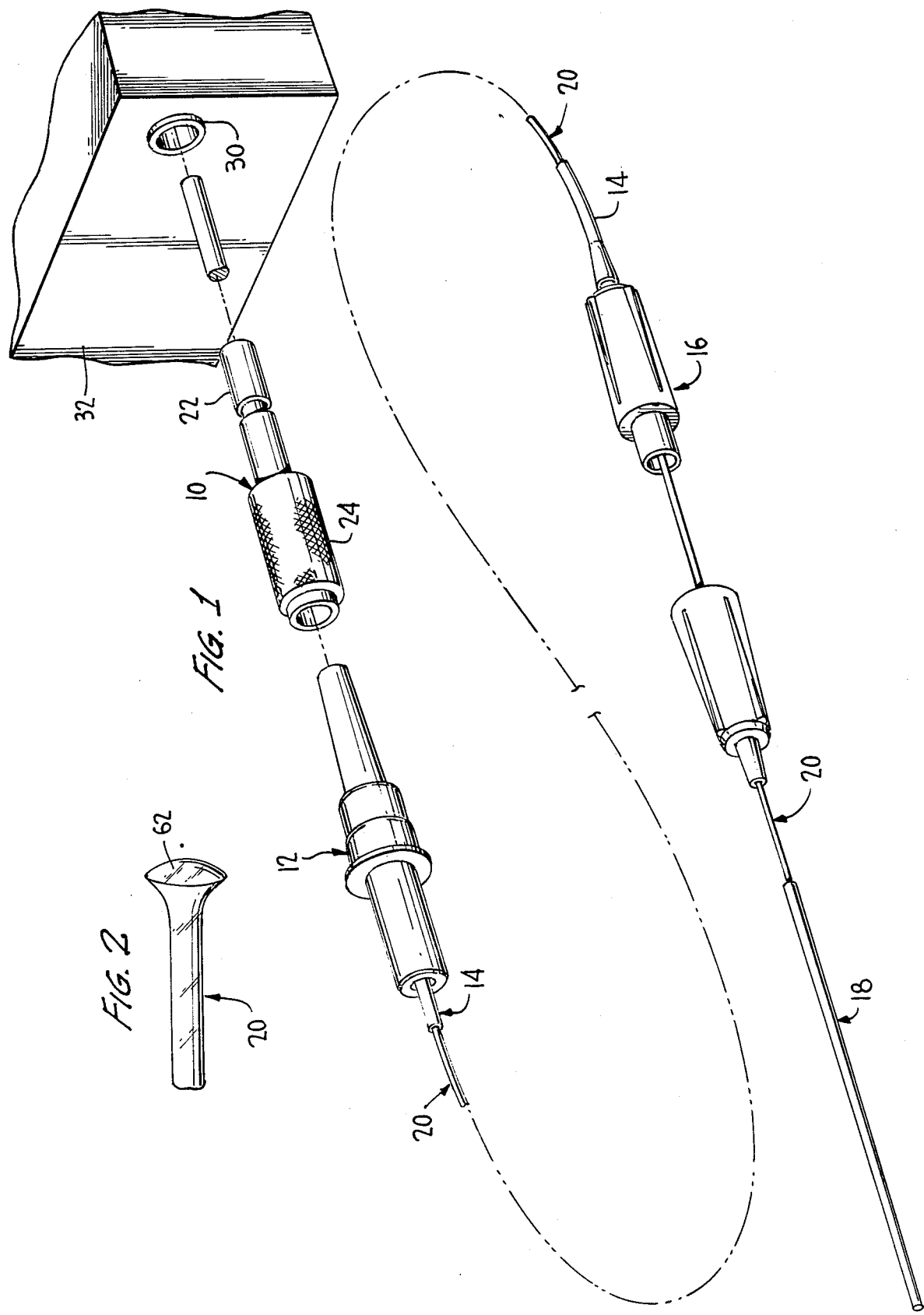

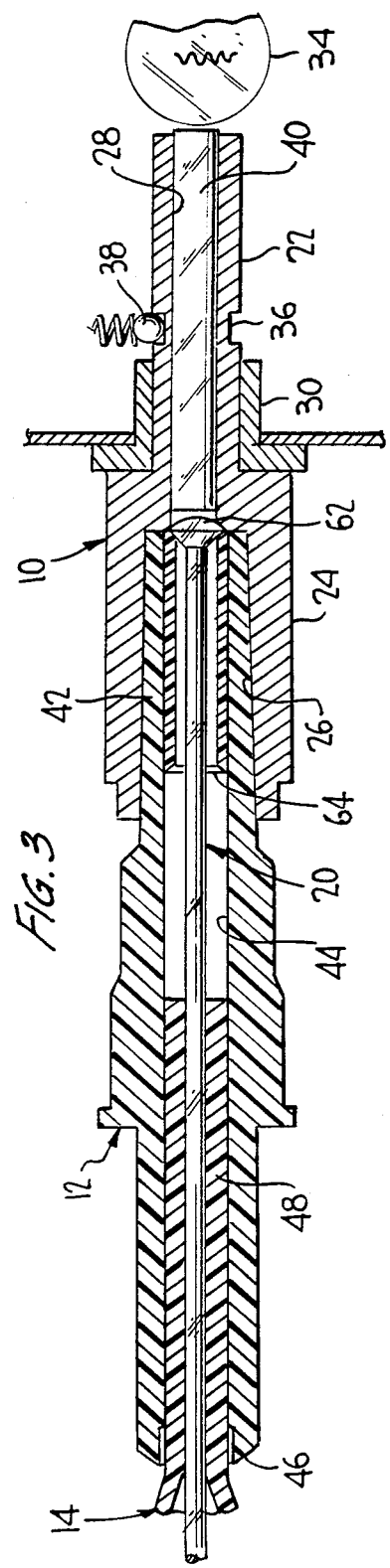
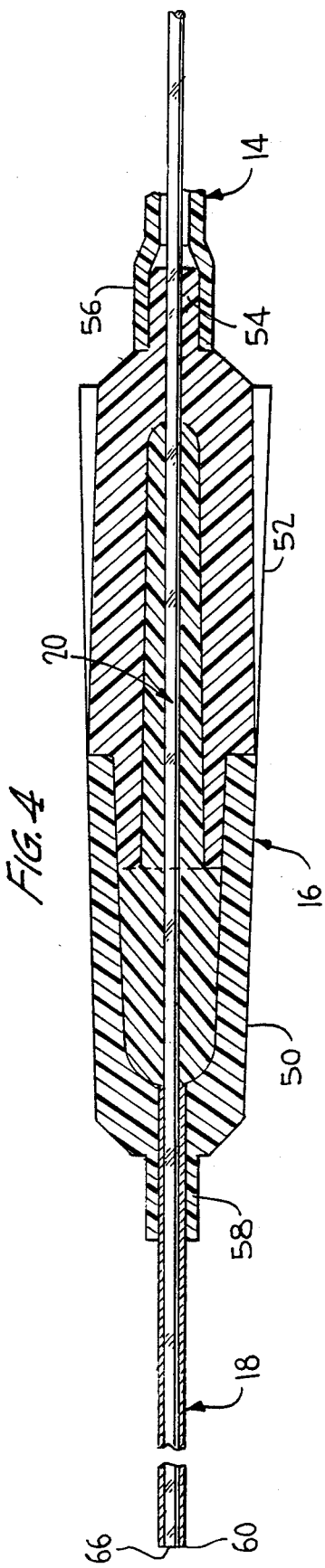

FIBER OPTIC ILLUMINATOR FOR USE IN SURGERY

BACKGROUND OF THE INVENTION

1. Field of the Invention

The present invention pertains to fiber optic illuminators and, more particularly, to fiber optic illuminators for use in surgery and designed to be economically disposable.

2. Discussion of the Prior Art

Illuminators are frequently utilized during surgery to provide adequate light for the surgeon, such illuminators being frequently used for ophthalmic surgery to direct light to various parts of the eye. In the past, light for ophthalmic operations has been available only from light sources in large pieces of equipment via expensive and complex light transmission systems having the disadvantages of being difficult to manipulate and requiring sterilization after use. U.S. Pat. No. 4,222,375 to Martinez is exemplary of attempts to simplify surgical illumination systems utilizing fiber optics; however, there remains a need for an economically disposable fiber optic illuminator for use with powerful light sources while shielding heat generated by the light sources and still minimizing light loss during transmission.

SUMMARY OF THE INVENTION

Accordingly, it is a primary object of the present invention to overcome the above mentioned disadvantages of the prior art by providing a fiber optic illuminator for use in surgery that is economically disposable and minimizes light losses.

Another object of the present invention is to utilize a light conducting rod to collect light from a light source while acting as a heat shield, the light conducting rod interfacing with a lens on the end of a strand of fiber optic plastic material having a distal end positioned at the distal end of a cannula to be held by a surgeon.

A further object of the present invention is to form a fiber optic illuminator for use in surgery of a minimal number of simply assembled components while providing maximum light transmission.

The present invention has an additional object in that a fiber optic element extends through a flexible tubing to minimize stray light and protect the fiber optic element from kinking and wearing due to contact to maximize light transmission.

Some of the advantages of the present invention over the prior art are that the fiber optic illuminator of the present invention is easily assembled of inexpensive components to be economically disposable, maximizes light transmission to the distal end of a cannula and prevents wear and tear on the fiber optic element.

The present invention is generally characterized in a fiber optic illuminator for use in surgery and adapted for use with a light source having an adjacent socket comprising an adapter having a body having a conical bore therein, a barrel extending from the body adapted to be received in the light source socket and having an axial bore therethrough communicating with the conical bore in axial alignment therewith, and a light conducting rod mounted in the barrel axial bore adapted to collect light from the light source, an interconnector having a first end with a conical configuration received in the conical bore in the adapter body, a second end and an axial bore through the interconnector, a support hub having a proximal end and a distal end, a cannula having a proximal end mounted in the distal end of the support hub and a distal end, a length of flexible tubing connected with the second end of the interconnector and with the proximal end of the support hub, and a fiber optic element having a proximal end supported at the first end of the interconnector and positioned adjacent the light conducting rod in the adapter and a distal end positioned at the distal end of the cannula, the fiber optic element passing through the interconnector axial bore, the flexible tubing, the support hub and the cannula whereby light from the light source is conducted to the distal end of the cannula via the light conducting rod and the fiber optic element.

Other objects and advantages of the present invention will become apparent from the following description of the preferred embodiment taken in conjunction with the drawings.

BRIEF DESCRIPTION OF THE DRAWINGS

FIG. 1 is an exploded view of a fiber optic illuminator in accordance with the present invention.

FIG. 2 is a broken perspective of the proximal end of a fiber optic element of the fiber optic illuminator of the present invention.

FIG. 3 is a cross section of the adapter and interconnector of the fiber optic illuminator of the present invention.

FIG. 4 is a cross section of the support hub and cannula of the fiber optic illuminator of the present invention.

DESCRIPTION OF THE PREFERRED EMBODIMENT

A fiber optic illuminator according to the present invention for use in surgery is illustrated in FIG. 1 and includes, as basic components, an adapter 10 designed to be received in a socket adjacent a light source, and interconnector 12 received in the adapter 10, a length of flexible tubing 14 connected with interconnector 12 and a support hub 16, a rigid cannula 18 mounted on the support hub and a fiber optic element 20 extending from the interconnector 12 through the tubing 14, the support hub 16 and the cannula 18. The fiber optic illuminator can be utilized with any suitable light source such as the light source available in the Ocutome Model 8000 manufactured by CooperVision.

The adapter 10, as shown in FIG. 3, includes a barrel 22 extending from a body 24 having a conical bore 26 therein, the barrel 22 having an axial bore 28 therethrough communicating with the conical bore in axial alignment therewith. The barrel has an outer configuration designed to be received in a socket 30 in a housing 32 for a light source 34, such as an incandescent lamp, the barrel having an annular groove 36 for receiving a ball detent 38 to maintain the barrel in place in the socket. A light conducting rod 40 is mounted in barrel axial bore 28 to have one end disposed adjacent light source 34 and an opposite end disposed adjacent the end of conical bore 26. The light conducting rod can be made of glass or fused fiber optic material and is secured in the barrel with silicone rubber glue to provide compensation for thermal expansion and contraction, it being noted that the light conducting rod and adapter will provide a heat sink or shield for the remaining components of the fiber optic illuminator. The adapter 10 is preferably made of aluminum with body 24 having a knurled outer surface.

Interconnector 12 has a conical end 42 to be received with a force fit in conical bore 26 of adapter 10 and has an axial bore 44 therethrough tapering from a widest point at an end 46 to a narrowest point at conical end 42.

A length of flexible translucent plastic tubing 14 has an end 48 received with a force fit in axial bore 44 in interconnector 12, the tubing 14 extending from the interconnector to support hub 16 formed of a hollow female component 50 and a hollow male component 52 having a nipple 54 extending therefrom and received in an end 56 of the flexible tubing 14. Rigid cannula 18 is mounted in a distal end 58 of the support hub formed by a nipple extending from the female component 50 and secured in place either by force fit or by a suitable adhesive, the cannula tapering from a larger diameter at the proximal end secured to the support hub to a smaller diameter at a distal end 60.

Fiber optic element 20 is preferably a single strand of fiber optic plastic material, such as Crofon manufactured by Dupont, and the proximal end 62 of the fiber optic element is heated or otherwise shaped to form a lens disposed at the end of interconnector 12 to be positioned adjacent light conducting rod 40. The fiber optic element is mounted in the axial bore in the interconnector 12 by means of a silicone rubber sleeve 64, and the hollow components of support hub 16 are filled with a silicone rubber self-curing potting material to secure fiber optic element 20 therein. The fiber optic element has an outer diameter less than the inner diameter of flexible tubing 14 to facilitate passage therethrough, and the fiber optic element passes through cannula 18 to terminate at a distal end 66 aligned with the distal end 60 of the cannula, the fiber optic element being maintained in position by the potting material in support hub 16.

The light conducting rod 40 has a diameter much larger than the fiber optic element 20 and collects a substantial amount of light from source 34 for transmission to lens 62 at the proximal end of the fiber optic element 20 while also functioning as a heat shield or sink. The lens 62 collects virtually all of the light from the light conducting rod, and only minimal light losses occur as the light is transmitted through the fiber optic element to its distal end due to the protection provided by flexible tubing 14. By making flexible tubing 14 translucent, the fiber optic illuminator will produce some stray light to permit it to be easily distinguished in a dark surgical operating room. To provide maximum light transmission, it is desirable to use a large diameter strand of fiber optic plastic material on the order of 0.030 inches; however, it is preferable to have a 20 gauge distal end of the cannula for surgical purposes which represents an inner diameter of 0.026 inches. To satisfy both of these conditions, the cannula is tapered from 19 gauge (inner diameter of 0.032 inches) at the proximal end to 20 gauge at the distal end, and the fiber optic element is stretched with the application of heat to reduce the diameter to fit in the cannula.

From the above, it will be appreciated that the fiber optic illuminator of the present invention is constructed of inexpensive, easily assembled and manufactured parts to be economically disposable while providing maximum illumination and being easy to handle by a surgeon.

Inasmuch as the present invention is subject to many variations, modifications and changes in detail, it is intended that all subject matter discussed above or shown in the accompanying drawings be interpreted as illustrative and not in a limiting sense.

What is claimed is:

1. A fiber optic illuminator for use in surgery and adapted for use with a light source having an adjacent socket comprising a reusable adapter having a body having a conical bore therein, a barrel extending from said body adapted to be received in the light source socket and having an axial bore therethrough communicating with said conical bore in axial alignment therewith, and a light conducting rod mounted in said barrel axial bore adapted to collect light from the light source;

a disposable interconnector having a first end with a conical configuration received with a force fit, in said conical bore in said adapter body to be removable a second end and an axial bore through said interconnector;

a disposable support hub having a proximal end and a distal end;

a disposable cannula having a proximal and mounted in said distal end of said support hub and a distal end;

a disposable length of flexible tubing connected with said second end of said interconnector and with said proximal end of said support hub; and a disposable fiber optic element formed of a single strand of fiber optic plastic material having a proximal end supported at said first end of said interconnector and positioned adjacent said light conducting rod in said adapter and a distal end positioned at said distal end of said cannula, said fiber optic element passing through said interconnector axial bore, said flexible tubing, said support hub and said cannula whereby light from the light source is conducted to said distal end of said cannula via said light conducting rod and said fiber optic element.

2. A fiber optic illuminator as recited in claim 1 wherein said fiber optic element has a lens formed on said proximal end.

3. A fiber optic illuminator as recited in claim 2 and further comprising a rubber sleeve disposed in said interconnector axial bore to mount said fiber optic element lens.

4. A fiber optic illuminator as recited in claim 3 wherein said flexible tubing extends into said interconnector axial bore.

5. A fiber optic illuminator as recited in claim 4 wherein said interconnector axial bore is conical.

6. A fiber optic illuminator as recited in claim 1 wherein said support hub is formed of a first hollow component mounting said cannula and a second hollow component mating with said first component and receiving said flexible tubing, one of said hollow first and second components having a portion received in the other of said hollow first and second components and said hollow first and second components being filled with a potting material to fix said fiber optic element in said support hub.

7. A fiber optic illuminator as recited in claim 1 wherein said flexible tubing is translucent.

8. A fiber optic illuminator as recited in claim 1 wherein said cannula is tapered from a larger diameter at said proximal end to a smaller diameter at said distal end and said strand of fiber optic plastic material is stretched to reduce its diameter to fit the length of said cannula.

* * * * *